(12) United States Patent
Yoshida et al.

(10) Patent No.: US 8,247,463 B2
(45) Date of Patent: Aug. 21, 2012

(54) METHOD OF COPRODUCING METHANOL AND AMMONIA

(75) Inventors: Nobuhiro Yoshida, Chiba (JP); Kunio Hirotani, Chiba (JP)

(73) Assignee: Toyo Engineering Corporation, Tokyo (JP)

( * ) Notice: Subject to any disclaimer, the term of this patent is extended or adjusted under 35 U.S.C. 154(b) by 296 days.

(21) Appl. No.: 12/653,149

(22) Filed: Dec. 9, 2009

(65) Prior Publication Data

US 2010/0150810 A1   Jun. 17, 2010

(30) Foreign Application Priority Data

Dec. 15, 2008   (JP) .................. 2008-318394

(51) Int. Cl.
*C07C 27/14*   (2006.01)
*C01C 1/04*   (2006.01)
(52) U.S. Cl. ........ 518/704; 518/703; 423/361; 423/359; 423/237; 252/373; 252/374
(58) Field of Classification Search .................... 518/703
See application file for complete search history.

(56) References Cited

U.S. PATENT DOCUMENTS 3,598,527 A   8/1971   Quartulli et al.
7,517,373 B2 *   4/2009   Sakai et al. .................. 48/127.9
2007/0299144 A1   12/2007   Davey et al.

FOREIGN PATENT DOCUMENTS

| DE | 33 36 649 A1 | 4/1985 |
| GB | 2084973 A * | 4/1982 |
| GB | 2 252 317 A | 8/1992 |
| JP | 55-154314 | 12/1980 |
| JP | 56-120514 | 9/1981 |
| JP | 06-234517 | 8/1994 |
| JP | 2000-063115 | 2/2000 |
| WO | WO 97/10194 | 3/1997 |

OTHER PUBLICATIONS

European Patent Office search Report dated Mar. 25, 2010 (6 pages).
Appl, Ammonia Methanol Hydrogen Carbon Monoxide—Modern Production Technologies, Nitrogen, CRU Publishing Ltd., pp. 74-85 (1997).
Fukuyama, "Toyo's JumboMeOH Technology", Speech, 11th IMPCA 2008 Asian Methanol Conference (May 2008).

* cited by examiner

*Primary Examiner* — Yate K Cutliff
(74) *Attorney, Agent, or Firm* — Flynn, Thiel, Boutell & Tanis, P.C.

(57) ABSTRACT

The present invention provides a process of coproducing methanol and ammonia by using natural gas, LPG, butane, or naphtha as a raw material, having a methanol production process (A) composed of specific steps and an ammonia production process (B) also composed of specific steps.

6 Claims, 3 Drawing Sheets

METHOD OF COPRODUCING METHANOL AND AMMONIA

TECHNICAL FIELD

The present invention relates to a technology for coproducing methanol and ammonia from synthesis gas obtained from reforming a hydrocarbon, such as natural gas, liquid petroleum gas, butane, naphtha and so on.

BACKGROUND ARTS

Both technologies for the production of methanol and for the production of ammonia use hydrogen as a main raw material and require technology to produce a synthesis gas containing hydrogen and carbon monoxide, and the production process of ammonia comprises sections derived from the technologies to produce a synthesis gas by reforming raw materials similar to those to produce a synthesis gas for methanol synthesis, and further includes a section to generate carbon dioxide and hydrogen by CO conversion of the synthesis gas formed by steam reforming, a section to remove carbon dioxide which is increased by an equal amount through the CO conversion, and a section to purify hydrogen to be suitable as a feedstock for ammonia synthesis by removing or inactivating the traces of remaining carbon monoxide and carbon dioxide. Thus, the primary reforming and/or the secondary reforming technologies of natural gas and the like can be utilized in common, and thereby various methods of the coproduction of methanol and ammonia have been conventionally proposed.

The raw materials required for producing methanol are hydrogen, carbon monoxide, and carbon dioxide, and these gases are the main components of a synthesis gas obtained by the steam reforming of a hydrocarbon, such as natural gas, LPG, butane or naphtha, and it is desired to have a ratio fulfilling the chemical stoichiometric formulas for methanol synthesis, which are:

(1)

(2), and it is ideal that the following R value, as the stoichiometrically-factored number, R=(mole number of $H_2$−mole number of carbon dioxide)/(mole number of CO−mole number of carbon dioxide)  (3)

is equal to 2, while the synthesis gas obtained from the steam reforming generally has the R value larger than 2 and is rich in hydrogen as compared to carbon.

In contrast, the raw materials required for producing ammonia are hydrogen and nitrogen, and it is important to adjust the flow ratio of hydrogen, which is a main component of the purified synthesis gas for ammonia synthesis, obtained by a purification method, in which carbon dioxide is removed from the synthesis gas obtained through CO conversion allocated after the steam reforming (primary reforming) and the oxygen reforming (secondary reforming) of a hydrocarbon, such as natural gas, LPG, butane or naphtha, in order to convert carbon monoxide to carbon dioxide for the essential removal of carbon dioxide by $CO_2$ absorption ($CO_2$ removal), and traces of remaining carbon monoxide and carbon dioxide are further separated at a low temperature or become inactive to ammonia synthesis catalyst by methanation, and nitrogen entrained by the purified synthesis gas, which is contained in the air used for the oxygen reforming (secondary reforming) and is an inert to the reforming reaction, is adjusted to the stoichiometric 3-to-1.

In conventional methods of coproducing methanol and ammonia, the following methods have been proposed of adjusting the flow ratio of hydrogen-to-nitrogen to 3-to-1.

JP-A 55-154314 (FIG. 1, lower right-handed column of page 2), describes a method of preparing synthesis gas for ammonia synthesis by adjusting the flow ratio of hydrogen and nitrogen in the purified synthesis gas, wherein the purge gas from a main methanol synthesis facility treated by the primary reforming and the secondary reforming prior to the high temperature CO conversion, the low temperature CO conversion, the $CO_2$ removal, the methanation further processing the remaining carbon monoxide and carbon dioxide, for the purpose of obtaining the stoichiometric ratio of 3-to-1 as a prior art. It describes that a method of producing ammonia that consumes less energy, by way of preparing the synthesis gas for ammonia synthesis by omitting the process of low temperature CO conversion and by the process of removing traces of carbon monoxide and carbon dioxide, which are catalyst poisons for an ammonia synthesis catalyst, not by the methanation process (2.5 MPa), but by an auxiliary methanol synthesis facility at a high pressure (from 10 to 30 MPa) applying that carbon monoxide and carbon dioxide become feedstocks for methanol synthesis of the reaction formulas (1) and (2) respectively.

In addition, in JP-A 56-120514, DE-A1 3336649, and GB-A 2252317 (Claim 1), methods of ammonia synthesis are disclosed in which, since the purge gas from the methanol synthesis facility described above is rich in hydrogen and can be equivalent to the reformed gas of the primary reformer in a conventional ammonia production process, it is possible to adjust the flow ratio of hydrogen and nitrogen in the synthesis gas to the stoichiometric ratio of 3-to-1 and also possible to reduce the energy consumption even when omitting the primary reformer from the conventional ammonia production process and using the purge gas only in the secondary reformer.

In JP-A 2000-63115 ([0006] [0011]), although a method is disclosed of coproducing methanol and ammonia by omitting the CO conversion section and providing the methanol synthesis section after the $CO_2$ removal section in a conventional method of producing synthesis gas for ammonia from natural gas, it is explicitly expressed that the amount of removing the carbonoxide components (carbon monoxide and carbon dioxide) is limited because carbon dioxide is removed without using a shift reactor which converts carbon monoxide into carbon dioxide. Thus, the method of coproducing methanol and ammonia is to be established in the case of a relatively high methanol production ratio and is generally applied to the case of producing a larger amount of methanol than ammonia in terms of weight ratio. In addition, it is almost impossible to produce only methanol or ammonia without remarkably decreasing the efficiency.

In JP-B2 7-33253, a method is disclosed of synthesizing a smaller amount of methanol than ammonia. It describes that in a conventional ammonia production process from natural gas, a compressed synthesis gas after methanation is drawn out from the synthesis gas in the middle stage of the compression section so as to make the ratio of hydrogen to nitrogen in the synthesis gas larger than 3, separating and extracting hydrogen for methanol synthesis by a membrane or the like, and mixing with carbon dioxide from the $CO_2$ removal section to be supplied to the methanol synthesis section.

In WO 97/10194, a method is disclosed of synthesizing methanol by bypassing a portion of the synthesis gas from the secondary reformer, in a conventional ammonia production process from natural gas, over the high temperature CO conversion section to put into the methanol synthesis section in one pass. Although the insertion of such a methanol synthesis section here exhibits the performance as an alternative for the CO conversion reaction at a high temperature and, at the same time, gives the characteristic of being capable of producing not just carbon dioxide but more useful methanol, the conversion rate of carbon to methanol is remarkably low due to the presence of the chemical equilibrium of the CO shift reaction. Thus, it becomes clear that the amount of methanol is too small to be referred to as coproduction of methanol and ammonia, which does not go beyond the sense of the language of by-production. Moreover, it is almost impossible to produce only methanol without remarkably decreasing the efficiency.

A method is generally known in which hydrogen gas containing a small amount of methane is obtained by removing carbon dioxide after recovering methanol contained in the purge gas and then, nitrogen obtained from an air separation unit is added to it so as to make the ratio of hydrogen to nitrogen to be 3-to-1, which thereby prepares a feedstock gas for ammonia synthesis as another method of producing ammonia by using purge gas rich in unreacted hydrogen from methanol synthesis facility as hydrogen source of feedstock.

In contrast, in the case of using an air separation unit, a balancing amount of utilized nitrogen and that of oxygen to be separated is important. US-A1 2007/0299144 discloses a method of using high-purity oxygen from air separation as a reforming agent of an autothermal reformer for synthesis gas production, in which a method is proposed such that the autothermally reformed gas is divided into two streams and carbon monoxide in one of the streams is subjected to CO conversion and is then removed as carbon dioxide, and thus hydrogen is obtained as a feedstock for ammonia synthesis and a portion of the hydrogen is mixed with the rest of the autothermally reformed gas, and thereby producing synthesis gas for methanol having the R value so-adjusted to be optimum for methanol synthesis and calculated by the formula (3) described above. At the same time, it is further possible to produce a synthesis gas for ammonia having the ratio of hydrogen to nitrogen of 3-to-1 by adding nitrogen obtained by air separation to the residual amount of the hydrogen as the feedstock for ammonia synthesis and free of carbon dioxide by the $CO_2$ removal, including the carbon dioxide converted from carbon monoxide through the CO conversion.

DISCLOSURE OF THE INVENTION

However, the conventional coproduction technologies described above have the following problems.

Since most of the conventional technologies described above use either a conventional methanol production process or a conventional ammonia production process as a principal process and the other synthesis process is brought in as a sub-process of the purge gas processing, or as a side-stream process or a partially alternative process in the synthesis gas purification process after the raw material reforming process. Those production methods are such that, as described above, the production amount of either one is remarkably small and can hardly be referred to as coproduction or can be referred to as by-production or that it is almost impossible to carry out the production of only either one.

In addition, because nitrogen is an inert gas for methanol synthesis, a synthesis gas for ammonia, for which the amount of nitrogen required is determined by the amount of air as an oxygen source for the secondary reformer, has an excessively large amount of unreacted hydrogen and carbon monoxide entrained by the purge gas from the methanol synthesis section, and causes both a low hydrogen conversion efficiency and a low carbon conversion efficiency.

On the other hand, carbon monoxide and carbon dioxide as the feedstock for methanol synthesis are catalyst poisons for ammonia synthesis. This fact prevents the synthesis gas production lines of both processes from sharing each other. Hence, the conventional technologies described above cannot be admitted at all as being superior in efficiency, in terms of the specific raw material consumption, as compared with single production of each of methanol and ammonia.

The present invention has been made in view of the problems of the conventional technologies described above, and it is an object to provide a method of coproducing methanol and ammonia, which can efficiently coproduce methanol and ammonia in terms of reactivity and economy, and can optionally select the single production of either one without being largely reduced in amount from the designed capacity of the equipment, and also can change the production ratio of methanol and ammonia almost without increasing or decreasing the specific raw material consumption.

A large amount of excess hydrogen is generated and used as fuel in a conventional methanol production process using natural gas as a raw material, while a large amount of carbon dioxide is by-produced in a conventional ammonia production process using natural gas as a raw material and carbon dioxide is released in the atmosphere when there is no adjacent urea plant. Therefore, the present inventors have come up with the idea that it becomes possible to increase the production of both methanol and ammonia considerably, even without increasing the design capacity of the desulfurization and the steam reforming in the methanol production unit and the desulfurization and the primary and secondary reformings in the ammonia production unit (that is, without increasing specific consumption of natural gas) by producing a synthesis gas for methanol, by way of directing the carbon dioxide by-produced in the ammonia production unit to the methanol production unit to be reacted with the excess hydrogen of the methanol production unit according to the formula (2) described above, and also by preparing a feedstock gas for ammonia synthesis, by way of further approximately purifying and separating the hydrogen remaining in the purge gas and combining it with the feedstock synthesis gas of the ammonia production unit, and thus they have reached the present invention enabling the coproduction of methanol and ammonia that uses a remarkably smaller amount of natural gas as compared with the case of independently producing each of methanol and ammonia.

Further, the present inventors also recovered recovering carbon dioxide to be emitted from an ammonia production unit and changing it into a methanol product. The present inventors intend the effective utilization of carbon dioxide, which is the main cause of global warming.

The present invention that achieves the objects described above is a process of coproducing methanol and ammonia, by using natural gas, LPG, butane or naphtha as raw material, including:

a methanol production process (A) having a steam reforming step (A-1) performing steam reforming of the raw material, a methanol synthesis step (A-2) reacting synthesis gas containing carbon monoxide, carbon dioxide and hydrogen formed in the steam reforming at the pressure of the methanol synthesis, a methanol condensation and separation step (A-3) condensing and gas-liquid separating a mixture containing the synthesized methanol and unreacted synthesis gas, and a hydrogen recovering step (A-4) recovering hydrogen contained in the gas portion of the condensed and gas-liquid separated mixture rich in hydrogen; and an ammonia production process (B) sequentially including a steam reforming step (primary reforming step) (B-1) performing steam reforming of the raw material, an air reforming step (secondary reforming step) (B-2) reforming unreformed methane remaining in the steam reformed gas with oxygen in the air by partially combusting a synthesis gas formed in the steam reforming step in order to provide the necessary heat of reaction for further methane reforming, the CO converting step (B-3) converting carbon monoxide in the synthesis gas formed in the air reforming step into carbon dioxide, the $CO_2$ removing step (B-4) recovering and removing carbon dioxide in the synthesis gas formed in the air reforming step and the CO converting step, a synthesis gas final purifying step (B-5) methanating traces of carbon monoxide and carbon dioxide further remaining in the synthesis gas to methane after the $CO_2$ removing step for being inert to ammonia synthesis, and the ammonia synthesis step (B-6) synthesizing ammonia from the finally purified synthesis gas at the ammonia synthesis pressure, wherein:

(1) directing the gas rich in hydrogen recovered in the hydrogen recovering step (A-4) in the methanol production process (A) to a certain step after the air reforming step (B-2) and before the ammonia synthesis step (B-6) in the ammonia production process (B) to prepare an additional feedstock gas for ammonia synthesis; and also (2) cooling the synthesis gas formed in the steam reforming step (A-1) in the methanol production process (A) and separating and removing condensed water from the cooled synthesis gas, mixing the water removed synthesis gas and carbon dioxide obtained by pre-compressing carbon dioxide obtained in the $CO_2$ removing step (B-4) in the ammonia production process (B), compressing the mixed synthesis gas and carbon dioxide up to the methanol synthesis pressure to be supplied as a reactant gas for methanol synthesis to the methanol synthesis step (A-2).

According to the present invention, it has advantages of being capable of making effective use of the purge gas from methanol synthesis and the off gas from ammonia synthesis, being capable of efficiently coproducing methanol and ammonia, and being further capable of optionally selecting the coproduction ratio of methanol and ammonia almost without increasing the specific raw material consumption even when singly producing either one of them or even when coproducing them by adjusting the amount of carbon dioxide supplied from the $CO_2$ removing step (B-4) to the methanol synthesis process.

BRIEF DESCRIPTION OF THE DRAWINGS

In the drawings, the reference symbol 101 means a steam reforming step, 102 means a methanol synthesis step, 104 means a methanol condensation and separation step, 105 means a hydrogen recovery step, 201 means a primary reforming step (steam reforming step), 202 means a secondary reforming step (air reforming step), 203 means a CO converting step, 204 means a $CO_2$ removing step, 205 means a synthesis gas final purifying step, 206 means an ammonia synthesis step, 207 means an ammonia condensing and separating step, and 301, 302, 303, 304, 305 and 306 mean compressors, respectively.

DETAILED DESCRIPTION OF THE INVENTION

The present invention is described below in detail.

Figure 1:
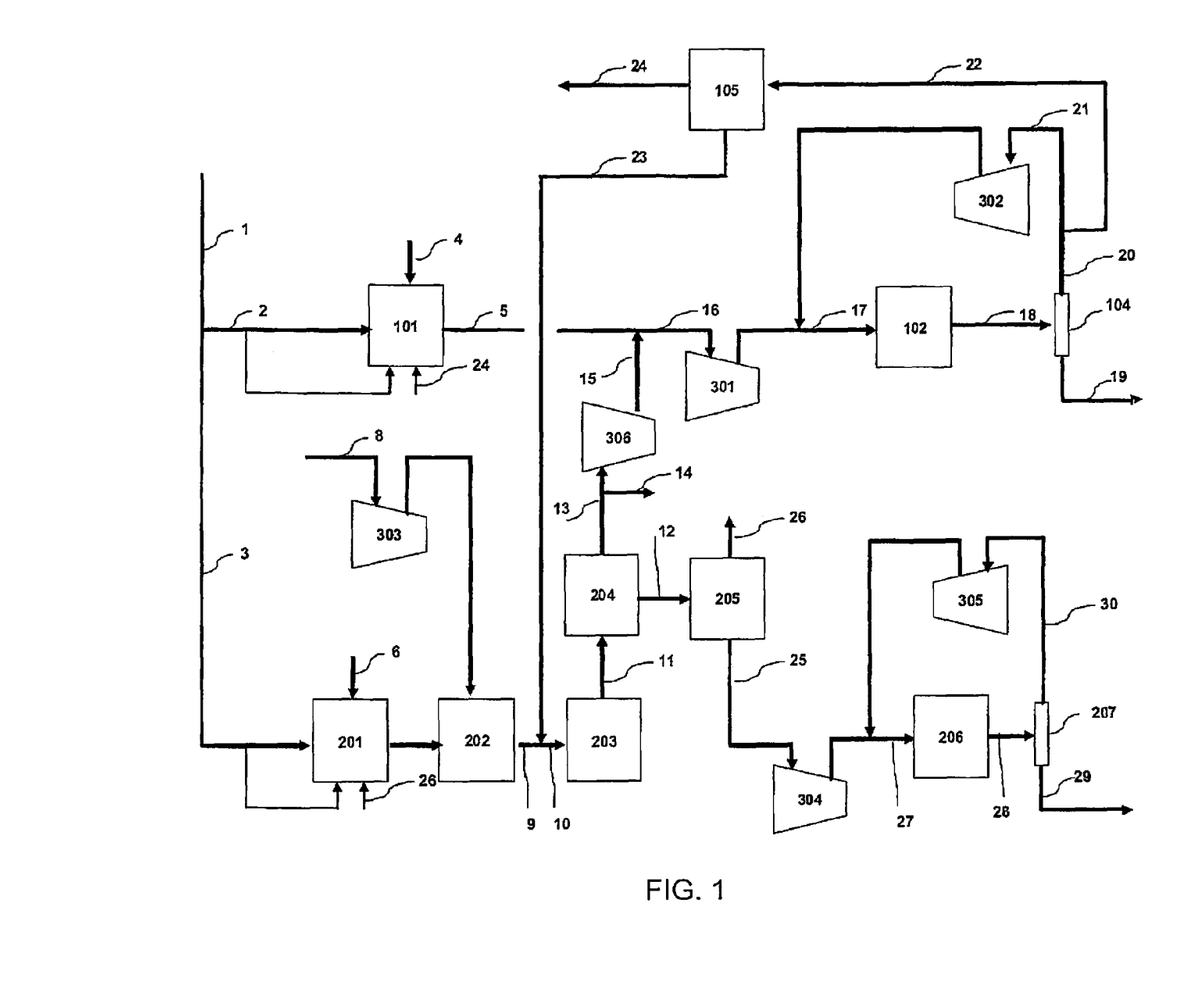
FIG. 1 is a process flow scheme showing one aspect of a process of the present invention.

An example of a process of coproducing methanol and ammonia according to a method of the present invention is shown in FIG. 1.

As a reactor used in the methanol synthesis process of the present invention, although any of the methanol synthesis reactors may be used which are, for example, introduced on pp. 75-84 in Reference Document 1 (written by Max Appl, Ammonia/Methanol/Hydrogen/Carbon Monoxide—Modern Production Technologies, 1997 CRU Publishing Ltd.: ISDN 1 873387 261), the present invention preferably uses the type that recovers the heat of reaction of methanol synthesis, in the form of steam generation, which is the basic principle common to those described in FIG. 77, FIG. 79, FIG. 80, FIG. 82 and FIG. 84 of the Reference Document 1.

Further, as the methanol synthesis reactor of the type of recovering the heat of reaction in the form of steam generation, the present invention more preferably uses such a reactor that is provided at least with boiler tubes surrounded by packed methanol synthesis catalyst and a center pipe for dispersion or collection of a reactant gas, and that has a configuration in which the reactant gas flows in the catalyst layers in the direction of the vessel diameter (radial flow), as described in FIG. 79 of the Document 1.

As understood from FIG. 1, gas 22, which is purged from the methanol synthesis step and contains excess hydrogen being separated in the gaseous phase of methanol condensation and separation step 104 and recovered by hydrogen recovering step 105, is divided into purge gas 23, rich in hydrogen and with a small amount of CO, and gas 24, rich in carbon monoxide with a small amount of hydrogen. A synthesis gas for ammonia is prepared by combining the above purge gas 23 rich in hydrogen with synthesis gas 9 to make the final reactant gas 10 for ammonia synthesis, where by converting most of the carbon monoxide contained in the line 10 to carbon dioxide with the CO shift reaction in the CO converting step 203, and most of the carbon dioxide is removed from the synthesis gas for ammonia in the carbon dioxide removing step 204. The removed carbon dioxide (line 15) is combined with synthesis gas 5 for methanol to prepare the reactant gas for methanol synthesis, and thereby it becomes possible to increase the production of both methanol and ammonia considerably even without increasing the design capacity of the desulfurization and the steam reforming step 101 in the methanol production process, and the desulfurization step, the primary reforming step 201 and the secondary reforming step 202 in the ammonia production process (that is, without increasing the amount of raw material natural gas), which enables the coproduction of methanol and ammonia that uses a remarkably small amount of raw material natural gas as compared with the case of independently producing each of methanol and ammonia.

In the flow scheme of FIG. 1, a raw material such as natural gas, in the flow path 1 is divided into a gas flow path 2 (a first feedstream) supplied to the steam reforming step 101 for the production of a synthesis gas for methanol and a gas flow path 3 (a second feedstream) supplied to the primary reforming step 201 for the production of a synthesis gas for ammonia, and the total amount of the raw material being subjected to reforming for the production of synthesis gases for methanol and for ammonia and the raw material as the fuels in the steam reforming step 101 and the primary reforming step 201 respectively flow to the flow path 2 and the flow path 3. The raw material in the flow path 3 are usually pressurized up to the reforming pressure considered as optimum for a synthesis gas for ammonia by a natural gas compressor (omitted from the figure), followed by going through the desulfurization step (omitted from the figure) and the primary reforming step 201. Here, by determining the amounts allocated to respective raw materials for the flow path 2 and the flow path 3, which can be set optionally, it is possible to determine the production amount in the case of the single production of methanol and ammonia.

It should be noted that it is possible to effectively utilize the final purge gas 24 from the methanol synthesis process and offgas 26 from the final purificating step 205 of the synthesis gas for ammonia as respective fuels in the reforming furnaces (24 and 26 are not necessarily required to be used only either for the steam reforming step 101 for the methanol synthesis gas or the primary reforming step 201 for the ammonia synthesis gas respectively, but in consideration of the overall fuel balance, the most appropriate fuel allocation to each reforming step may be carried out), and thus it is possible to reduce the amount of natural gas as the overall fuel.

To the reforming step 101 for the methanol synthesis gas and the primary reforming step 201 for the ammonia synthesis gas 7, the steam lines 4 and 6 for reforming are added respectively, and carbon monoxide and hydrogen are formed by the following steam reforming reactions.

$$C_mH_n + mH_2O \rightarrow mCO + (m+n/2)H_2 \quad (4)$$

$$CH_4 + H_2O = CO + 3H_2 \quad (5)$$

The formula (4) is in chemical equilibrium with the formula (5) regarding methane, and approximately from 2% to 10% of the methane usually remains depending on the operating conditions of the reforming step, and since the remaining methane is accumulated in closed process systems (synthesis loops) composed of the methanol synthesis step 102 and the ammonia synthesis step 206, the condensation and separation processes 104 and 207, and the recycle compressors 302 and 305 as respective inert gases for methanol synthesis and ammonia synthesis, it is necessary to purge out a portion of the gases separated from the condensed liquid in the synthesis loops. Since a large amount of purge leads to a loss of the unreacted synthesis gas, to decrease the synthesis efficiency and, further, to deteriorate the specific raw material consumption, the amount of the remaining methane in the reforming step is preferably as small as possible. In addition, in the steam reforming step 101 for the methanol synthesis gas 5 and the primary reforming step 201 for the ammonia synthesis gas, the CO shift reaction of the formula (6) below is also in chemical equilibrium at the same time.

$$CO + H_2O = CO_2 + H_2 \quad (6)$$

Since the ammonia synthesis is represented by the formula (7) below and requires $N_2$ as a raw material, air 8 equivalent to the required $N_2$ is pressurized up to the reforming pressure by using air compressor 303 to be introduced to the secondary reforming step 202.

$$N_2 + H_2 = NH_3 \quad (7)$$

Since the combustion of hydrogen mainly occurs due to the oxygen in the air in the secondary reforming step leading to the exposure to a rather high temperature (approximately 1000° C. at the reactor outlet) as compared with the primary reforming step, the chemical equilibrium in the formula (5), which is an endothermic reaction, is shifted in the direction of methane reduction. Thus, the influence of methane that becomes an inert gas in the ammonia synthesis loop described above can be reduced.

The crude synthesis gas 9 for ammonia synthesis supplied from the secondary reforming step 202 is subjected to heat recovery and cooling to separate condensed water (omitted from the figure), and then is introduced to the CO converting step 203 as the reactant gas 10 for ammonia synthesis mixed with the gas 23, rich in hydrogen with a small amount of carbon monoxide, recovered from the purge gas for methanol synthesis. In the CO converting step 203, carbon monoxide is removed as much as possible which becomes a catalyst poison for ammonia synthesis by the CO shift reaction of the formula (6). It should be noted that, when the CO concentration in the purge gas for methanol synthesis is very small to the extent of not demanding the necessity of the CO shift reaction, the flow path 23 may also be mixed with the flow path 11, which is the outlet of the CO converting step 203. Further, if the carbon dioxide concentration as well as the carbon monoxide concentration is also extremely low in the purge gas for methanol synthesis, it may also be mixed with the flow path 12, which is the outlet of the $CO_2$ removing step 204, or with the outlet flow path 25 of the synthesis gas final purifying step 205.

The CO shift reaction is an exothermic reaction, and the lower the temperature, the less the amount of carbon monoxide residue. Thus, the reactor often has a configuration in which a cooler is placed in the middle for a multistage arrangement or cooling coils are disposed inside. It should be noted that, in the case where the steam 6 for primary reforming is insufficient as the steam for CO conversion, it is effective to introduce an increased amount of the steam 6 for prevention of carbon precipitation in the primary reforming step, while the increased amount may also be mixed after raising the temperature of the flow 10 (omitted from the figure).

The CO-converted synthesis gas from the CO converting step 203 is subjected to heat recovery and cooling to separate condensed water (omitted from the figure), followed by being directed to the $CO_2$ removing step 204 and carbon dioxide, which becomes a catalyst poison for ammonia synthesis, is removed. The $CO_2$ removing step 204 generally uses a system in which a solvent selectively absorbing carbon dioxide at a high pressure is used in regeneration and circulation at low pressure, and carbon dioxide having high purity is taken out as the flow 13.

The high purity carbon dioxide flow 13 taken out from the $CO_2$ removing step 204 is, in the case where the ratio of methanol coproduction is desired to be minimum, released out of the system in the total amount as the flow 14. In addition, in the case where the ratio of methanol coproduction is desired to be maximum, when the flow 13 is pressurized by the compressor 306 up to the pressure capable of being mixed with the flow of the synthesis gas 5 for methanol synthesis after heat recovery and cooling from the steam reforming step 101 and separation of condensed water (omitted from the figure) for production of a synthesis gas for methanol and thus becoming the flow 15 to be mixed with synthesis gas 5 to the flow 16, the amount of the unnecessary carbon dioxide equivalent is released and removed from the flow 13, as needed, as the flow 14 out of the system such that the stoichiometric ratio R of the formula (3) does not become less than 2. Here, by adjusting the amount of the carbon dioxide flow 15, it is theoretically possible to adjust the ratio of coproducing methanol and ammonia without increasing the specific raw material consumption. It should be noted that, although in reality variations in a loss of hydrogen going into the fuel gas 24 and the like have an influence due to the influence of minor changes in the mechanical efficiency caused by the amount of the carbon dioxide processed by the compressor to be used or the separation efficiency caused by the amount of the purge gas processed in the hydrogen recovering step 105 in the methanol production process, it can be estimated in the ordinal manner of those skilled in the art that the difference in the overall energy balance falls within 1% or less.

The flow 16 mixed as described above is pressurized up to a synthesis pressure (from 5 to 10 MPa) for methanol synthesis by a compressor 301, and is further mixed with an unreacted synthesis gas 21 to be recycled, followed by raising the temperature up to a methanol synthesis reaction starting temperature (approximately 210° C. to 240° C.) to be directed to the methanol synthesis step 102.

As a reactor to be used for the methanol synthesis step 102, often used is the adiabatic quench type, which is a method in which, by supplying a portion of a synthesis gas at a low temperature to be supplied to the reactor in between (a plurality of) catalyst layers by bypassing at least the first catalyst layer, the reactant gas containing an unreacted synthesis gas coming out from the first catalyst layer at a high temperature due to the heat of reaction is cooled and thereby the temperature of the gas to be supplied to each catalyst layer of the second catalyst layer and below is kept at the level suitable for initiating the reaction, as disclosed in FIG. 74 and FIG. 75 in the Reference Document 1 mentioned above, or the indirect cooling type, which is a method in which, by sequentially providing a heat exchanger between the first catalyst layer and the second catalyst layer and also further between the following catalyst layers, the temperature of the gas to be supplied to each catalyst layer of the second catalyst layer and below, is kept at the level suitable for initiating the reaction, as disclosed in FIG. 78 in the Reference Document 1 mentioned above. However, in the present invention, it is possible to increase the amount of ammonia production even more in the case of using a type of reactor of recovering the heat of reaction for methanol synthesis in the form of steam generation, as easily understood by those skilled in the art, which is another mode of the indirect cooling type and has the characteristics in which the one pass conversion rate is large while the amount of the purge gas in the synthesis loop becomes relatively large due to the requirement of mass balance, described in FIG. 77, FIG. 79, FIG. 80, FIG. 82, and FIG. 84 in the Reference Document 1 mentioned above.

More preferably, the amount of the catalyst to be used becomes minimum in the case of using a reactor, as one of the steam generation type reactors, having the characteristics of being capable of designing the temperature of operation at each point of the catalyst layers where the methanol synthesis reaction occurs so as to respectively have the maximum value of the reaction rate of methanol synthesis as disclosed in the temperature distribution described in Reference Document 2 (speech by Hiroshi Fukuyama in 11th IMPCA 2008 Asian Methanol Conference preprints, Kuala Lumpur, Malaysia, 20-22 May 2008, FIG. 13) because of the structure being provided at least with boiler tubes for generating steam surrounded by packed methanol synthesis catalyst and a center pipe for dispersion or collection of a reactant gas and having a configuration in which the reactant gas flows in the catalyst layers in the direction of the vessel diameter (radial flow), as described in FIG. 79 in the Reference Document 1 mentioned above.

The outlet flow 18 from the methanol synthesis process 102 is subjected to heat recovery and condensation of the liquid in the methanol condensation and separation step 104 to separate the crude methanol 19 from the unreacted synthesis gas 20, and the crude methanol 19 is sent to the methanol purifying step (omitted from the figure). In addition, in order that the inert gas (residual methane, nitrogen, and argon) in the unreacted synthesis gas 20 not accumulate in the methanol synthesis loop, an adequate amount of the purge 22 is purged out from the unreacted synthesis gas 20, and the flow 21 is compressed by the recycle compressor 302 and is mixed with the supply gas 17 to the methanol synthesis step 102 to be recycled.

Although the unreacted hydrogen, carbon monoxide, and carbon dioxide are contained in the purge 22 from the methanol synthesis loop, since, among them, hydrogen can be used as a feedstock gas for ammonia synthesis, hydrogen is recovered as much as possible via the hydrogen recovering step 105. In the hydrogen recovering step 105, it is considered that membrane separation using a hydrogen permeable function membrane, pressure swing adsorption separation (PSA), or the like is employed. The purge gas 23 rich in hydrogen thus obtained is used in circulation as a synthesis gas for ammonia, and the rest is used as the fuel 24 in the steam reforming step 101 for the production of a synthesis gas for methanol or as the fuel 26 in the primary reforming step 201 for the production of a synthesis gas for ammonia synthesis.

The synthesis gas from which carbon dioxide is absorbed and removed by the $CO_2$ removing step 204 from the crude synthesis gas for ammonia synthesis is directed to the synthesis gas final purifying step 205 in which a trace of remaining carbon monoxide and carbon dioxide are converted into methane, which is inert to the ammonia synthesis catalyst, by the methanation reaction represented by the formulas (8) and (9) below. In the synthesis gas final purifying step 205, a cryogenic separation unit, which removes other inert gases such as methane and argon introduced from the air used in the secondary reforming step, together with the traces of remaining carbon monoxide and carbon dioxide, or a device called a purifier may also be used. Alternatively, the methanation reaction and the cryogenic separation unit or the purifier mentioned above may also be combined. It is common to adsorb and remove the very traces of carbon dioxide still remaining after passing through the $CO_2$ removing step at the same time in an adsorption removal unit for traces of the moisture provided in a front stage of the unit for prevention of solidification in the cryogenic separation unit, and to distill and separate traces of other inert gases, such as carbon monoxide, methane, and argon, at extremely low temperature. The use of these devices enables the making of the amount of the purge gas from the ammonia synthesis loop to be extremely small.

$$CO + 3H_2 \rightarrow CH_4 + H_2O \qquad (8)$$

$$CO_2 + 4H_2 \rightarrow CH_4 + 2H_2O \qquad (9)$$

Although the purified synthesis gas obtained from the final purifying step 205 is required to adjust the loss of hydrogen and nitrogen dissolved and dissipated in the crude ammonia liquid, it is in principle nothing but a mixed gas of hydrogen and nitrogen in the stoichiometric amount of ammonia synthesis.

Since the amount of nitrogen that is uniquely determined by equilibrium in accordance with the operating temperature of the device is contained in the purge gas 26 containing carbon dioxide, carbon monoxide, and methane released from the final purifying step 205, the amount of air introduced in the flow 8 is to be corrected with the amount of nitrogen lost here from the stoichiometric value for introduction. The purge gas 26 may also be used as the fuel in the primary reforming step 201 producing a synthesis gas for ammonia.

The purified synthesis gas 25 is pressurized up to the synthesis pressure (from 9 to 15 MPa) for ammonia synthesis by a synthesis compressor 304 and is further mixed with the unreacted synthesis gas 30 to be recycled, followed by raising the temperature up to the ammonia synthesis reaction initiating temperature (from 400° C. to 500° C., approximately) and being directed to the ammonia synthesis step 206. The outlet flow 28 from the ammonia synthesis step 206 is subjected to heat recovery and condensation of the liquid (omitted from the figure) to separate the crude ammonia liquid 29 and the unreacted synthesis gas 30 in the condensing and separating step 207 and the crude ammonia liquid 29 is sent to the ammonia refrigeration and purification step (omitted from the figure). In addition, the unreacted synthesis gas 30 is recycled by the recycle compressor 305 and is added to the supply gas 27 to the ammonia synthesis step.

EXAMPLES

The present invention will be described in further detail below based on Examples. However, the present invention is not limited by the Examples.

Example 1

In the flow scheme of FIG. 1, natural gas having the composition of Table 1 is supplied through the flow path 1 to a process for coproducing methanol and ammonia.

TABLE 1

Composition of Raw Material Natural Gas (Lower Heating Value: 861.57 MJ/kmol)

|  | mol % |
|---|---|
| Methane | 82.64 |
| Ethane | 7.56 |
| Propane | 2.12 |
| Isobutane | 0.59 |
| n-butane | 0.57 |
| n-pentane | 0.49 |
| Carbon Dioxide | 5.38 |
| Nitrogen | 0.65 |
| Total | 100.00 |

Table 2, Table 3 and Table 4 show the mass balance of the Example. The left column indicates the number of each line shown in FIG. 1, and the top rows indicate the pressure, the temperature, the flow rate, and/or the composition flowing in each line.

TABLE 2

| Number | Pressure Mpa | Temperature ° C. | Flow Rate kmol/hr | Notes |
|---|---|---|---|---|
| 1 | 2.58 | 25 | 8219 | |
| 2 | 2.58 | 25 | 4050 | as raw material |
|   |      |    | 1453 | as fuel |
| 3 | 2.58 | 25 | 2522 | as raw material |
|   |      |    | 194  | as fuel |

TABLE 3

| Number | Pressure MPa | Temperature ° C. | $CH_4$ | CO | $CO_2$ | $H_2$ | $O_2$ | $N_2+Ar$ | $CH_3OH$ | $NH_3$ | $H_2O$ | Flow Rate Kmol/hr |
|---|---|---|---|---|---|---|---|---|---|---|---|---|
| 4 | 2.95 | 273 | | | | | | | | | 100 | 12,995 |
| 5 | 2.00 | 875 | 2.1 | 10.7 | 5.7 | 49.0 | | 0.1 | | | 32.4 | 25,741 |
| 6 | 4.62 | 355 | | | | | | | | | 100 | 7,572 |
| 7 | 4.07 | 713 | 15.2 | 2.5 | 6.7 | 26.3 | | 0.3 | | 0.0 | 49.1 | 12,095 |
| 8 | 0.10 | 40 | | | 0.0 | | 20.8 | 78.6 | | | 0.5 | 4,882 |
| 9 | 3.91 | 883 | 1.3 | 7.5 | 6.2 | 32.0 | | 19.8 | | 0.1 | 33.1 | 19,567 |
| 10 | 3.91 | 371 | 1.6 | 7.2 | 5.9 | 35.6 | | 18.6 | | 0.1 | 31.1 | 20,834 |
| 11 | 3.74 | 70 | 2.1 | 0.3 | 16.8 | 55.6 | | 24.3 | | 0.1 | 0.8 | 15,935 |
| 12 | 3.64 | 50 | 2.5 | 0.4 | 0.0 | 67.3 | | 29.5 | | 0.0 | 0.3 | 13,104 |
| 13 | 0.18 | 40 | | | 95.8 | 0.2 | | 0.0 | | | 4.0 | 2,716 |
| 14 | 0.18 | 40 | | | 95.8 | 0.2 | | 0.0 | | | 4.0 | 1,763 |
| 15 | 2.00 | 45 | | | 99.3 | 0.2 | | 0.0 | | | 0.5 | 953 |
| 16 | 1.79 | 45 | 2.9 | 14.9 | 13.0 | 68.8 | | 0.2 | | | 0.2 | 18,358 |
| 17 | 8.05 | 240 | 18.8 | 7.2 | 10.0 | 62.3 | | 1.0 | 0.6 | | 0.1 | 119,369 |
| 18 | 8.00 | 265 | 20.4 | 5.5 | 9.0 | 57.3 | | 1.1 | 4.8 | | 2.0 | 110,129 |
| 20 | 7.78 | 45 | 21.7 | 5.8 | 9.5 | 61.1 | | 1.2 | 0.7 | | 0.1 | 103,230 |
| 21 | 7.78 | 45 | 21.7 | 5.8 | 9.5 | 61.1 | | 1.2 | 0.7 | | 0.1 | 101,011 |
| 22 | 7.78 | 45 | 21.7 | 5.8 | 9.5 | 61.1 | | 1.2 | 0.7 | | 0.1 | 2,219 |
| 23 | 3.91 | 45 | 5.8 | 1.4 | 2.3 | 90.2 | | 0.3 | | | | 1,267 |
| 24 | 0.50 | 45 | 47.9 | 13.1 | 21.3 | 15.0 | | 2.6 | | | 0.1 | 782 |
| 25 | 3.17 | 1.8 | | | | 74.8 | | 25.2 | | | | 11,968 |
| 26 | 3.17 | 1.8 | 25.1 | | | 8.4 | | 66.5 | | | | 1,521 |
| 27 | 15.44 | 209 | | | | 70.0 | | 26.4 | | 3.6 | | 42,292 |
| 28 | 15.17 | 443 | | | | 57.7 | | 22.8 | | 19.5 | | 36,664 |
| 30 | 15.02 | 0 | | | | 68.1 | | 26.9 | | 5.0 | | 31,024 |

TABLE 4

| Number | Pressure MPa | Temperature °C. | Composition (weight %) | | | | Flow Rate t/day |
|---|---|---|---|---|---|---|---|
| | | | CH$_3$OH | NH$_3$ | Others | H$_2$O | |
| 19 | 7.8 | 45 | 76.1 | | 3.9 | 19.4 | 4623 |
| 29 | 15.02 | 0 | | 99.2 | 0.8 | | 2300 |

In this example, assuming that the loss and the like in the conventional recovery of methanol entrained in the purge gas and distillation purification of crude methanol is 1.5%, the methanol production capacity is estimated as 3465 t/day. Likewise, the ammonia production capacity in this example becomes 2300 t/day.

From the description above and Table 2, the specific natural gas consumption of this process for coproducing methanol and ammonia becomes 29.5 GJ/t−(methanol+ammonia).

In addition, when the utility mass balance of the process for coproducing methanol and ammonia in this example is calculated in a method ordinarily used by those skilled in the art for summarization, the specific utility consumptions in Table 5 are obtained.

TABLE 5

Specific utility Consumption of a Process for Coproducing 3456 t/day of Methanol and 2300 t/day of Ammonia

| | Utility Consumption/ t-(Methanol + Ammonia) |
|---|---|
| Electrical Power | 19.4 kWh |
| Cooling Water | 152 t |
| Boiler Supply Water | 0.98 t |
| 3 MPa Steam | 0.22 t |

Example 2

Figure 2:
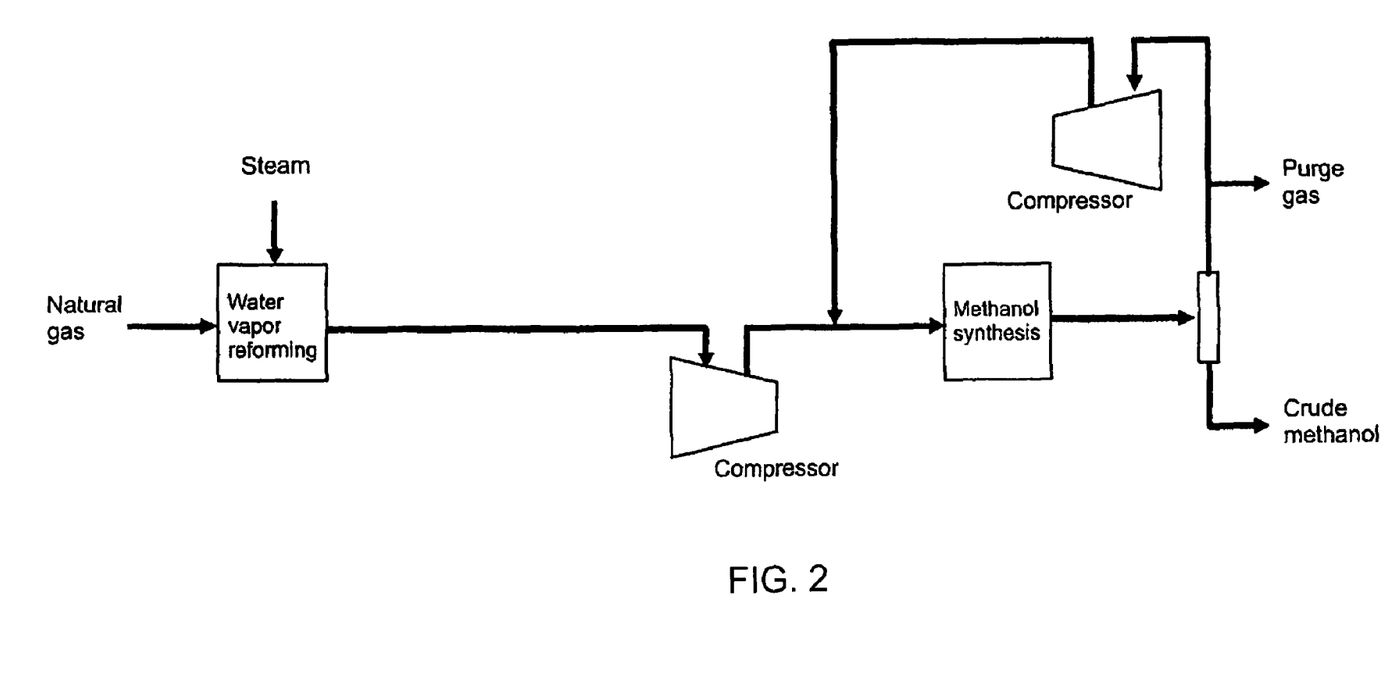
FIG. 2 is a conventional process flow scheme showing methanol production using natural gas as a raw material.
Figure 3:
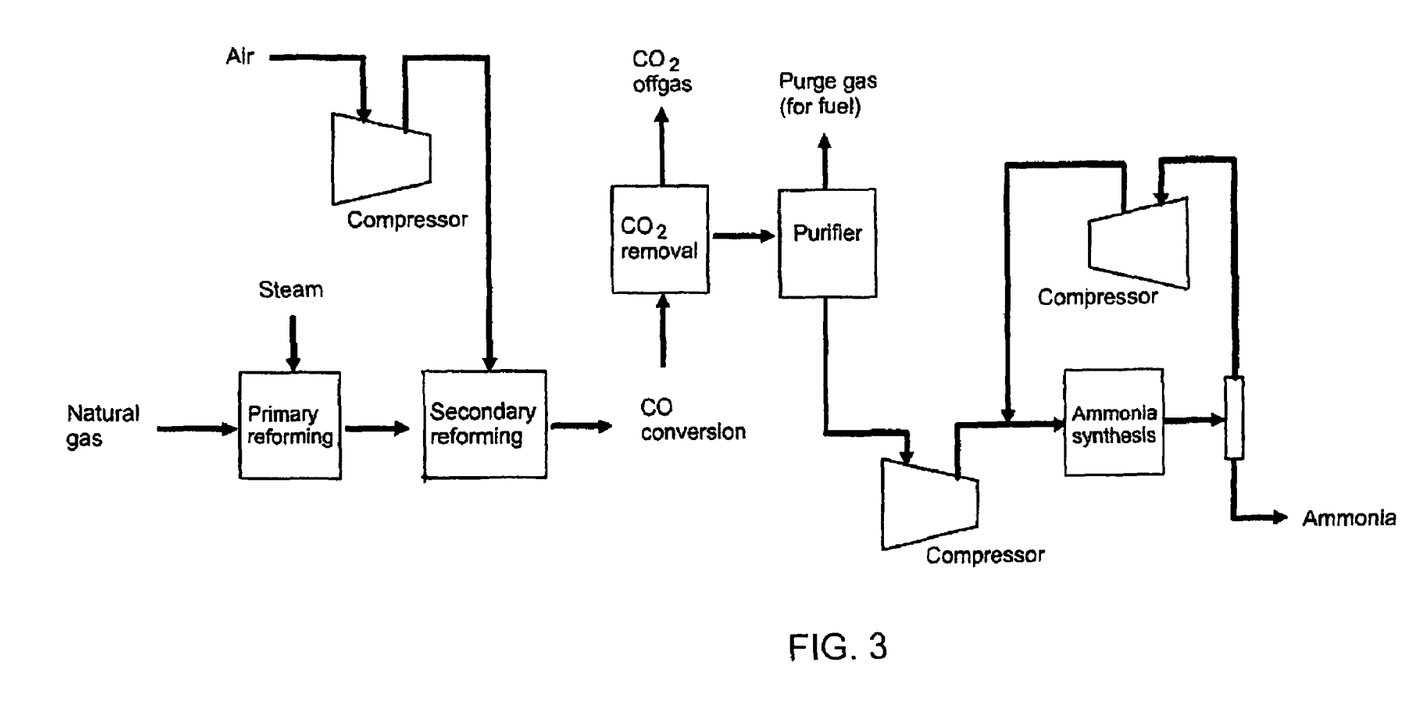
FIG. 3 is a conventional process flow scheme showing ammonia production using natural gas as a raw material.

In a methanol process shown by the flow scheme of FIG. 2 using 4050 kmol/hr of natural gas as raw material and an ammonia process shown by the flow scheme of FIG. 3 using 2522 kmol/hr of natural gas as a raw material, each natural gas being the amount equal to that of Example 1 described above, when the mass balance is calculated in the case of not using the carbon dioxide, which is removed in the ammonia process, for the methanol process, the amount of methanol production is naturally 3000 t/day, and as a conclusion of a standard balance calculation by those skilled in the art, it is determined that the amount of ammonia production is 2765 t/day, and the amounts of methanol and ammonia are the same as those of the Example 1 on a weight basis. In addition, it is also calculated that the specific consumptions of natural gas are also the same as that of the Example 1. Likewise, it becomes clear that the present invention provides a remarkable energy saving effect as compared with the case when each process produces methanol and ammonia independently. Likewise, from the mass balance in the case that 477 kmol/hr, which is half of the Example, of carbon dioxide among that removed in the ammonia process is used in the methanol process, it is determined that the amount of methanol production is 3232 t/day and of ammonia is 2548 t/day. That is, as an effect of the present invention, it is clear that the carbon dioxide removed in the ammonia process adjusts the ratio to be used as a raw material for methanol synthesis and thereby it is possible to carry out an adjustment of the amounts of producing methanol and ammonia without increasing or decreasing the raw material natural gas.

Comparative Example 1

Next, in a methanol process shown by the flow scheme of FIG. 2 using 4050 kmol/hr of natural gas as a raw material and an ammonia process shown by the flow scheme of FIG. 3 using 2522 kmol/hr of natural gas as a raw material, each natural gas being an equivalent amount to that of Example 2 described above, when the mass balance is calculated independently for each process, as a standard conclusion by those skilled in the art, it is respectively derived to be 3000 t/day of methanol and 2000 t/day of ammonia. When calculating the utility consumption in the same way as Example 1 to summarize the specific consumption of natural gas and the specific utility consumption, Table 6 is obtained. This example shows that, as compared with Example 1, the specific natural gas consumption is inferior by 9% and twice the amount of steam consumption is required, and it becomes clear that the present invention provides a remarkable energy saving effect as compared with the case of producing methanol and ammonia independently.

TABLE 6

Specific Unit Consumption of Process of 3000 t/day of Methanol and 2000 t/day of Ammonia

| | Methanol Process Unit Consumption/hr | Ammonia Process Unit Consumption/hr | Unit Consumption/t (Methanol + Ammonia) |
|---|---|---|---|
| Natural Gas | 4567 kmol | 3212 kmol | 32.2 GJ |
| Electrical Power | 3486 kWh | 551 kWh | 19.4 kWh |
| Cooling Water | 14587 t | 17137 t | 152 t |
| Boiler Supply Water | 115.3 t | 169.0 t | 1.36 t |
| 3 MPa Water Vapor | 0 t | 98.9 t | 0.47 t |

Reference Example 1

In the methanol synthesis step 102 in FIG. 1 in Example 1 described above, given that methanol is produced in the same amount using a catalyst in the same amount as the amount of the catalyst required in the case of employing a reactor, as the reactor to which the mass balance shown in Table 3 is given, removing the heat of reaction in the form of steam generation by indirectly cooling a large number of reaction tubes that supply the boiler water to the shell side and are packed with the catalyst, when using a reactor having the characteristics of being capable of designing the temperature of operation at each point of the catalyst layers where the methanol synthesis reaction occurs so as to respectively have the maximum value of the reaction rate of methanol synthesis, at least the mass balance of the synthesis loops shown in Table 7 and Table 8 is obtained as easily estimated by those skilled in the art because of the structure provided with boiler tubes for generating steam surrounded by packed methanol synthesis catalyst and a center pipe for the dispersion or accumulation of a reactant gas and having a configuration in which the reactant gas flows in the catalyst layers in the direction of the vessel diameter (radial flow). In this example, the synthesis pressure required for the flow path 18 is 7.0 MPa and it achieves a synthesis pressure lower by 1.0 MPa than 8.0 MPa given in Table 3. Therefore, a result is obtained that the power requirements of the synthesis compressor can be reduced by selecting a type of methanol synthesis reactor, and it is possible to enhance the energy saving effect of the present invention even more. Here, if the methanol synthesis is performed at the same synthesis pressure, the reaction proceeds even more inside the reactor and the methanol concentration in the flow path 18 increases and thus, more of the purge gas has to be used in order to prevent the inert gas from accumulating inside the synthesis loop and the amount of recycled synthesis gas becomes smaller and, as a result, it can also be calculated easily that the amount of unreacted hydrogen entrained by the purge gas is increased. This means that, instead of the amount of methanol production becoming smaller, the amount of hydrogen in the purge gas rich in hydrogen used for ammonia synthesis is increased and the amount of ammonia production can be increased. In other words, to certain restrictive conditions, that is, a practical problem of coproducing methanol and ammonia in not less than a certain capacity while taking into consideration the upper limit value of using an expensive catalyst and the maximum value of the synthesis pressure at which inexpensive device materials can be used, it is possible to give a solution to make an allowance for the production ratio of methanol and ammonia.

TABLE 7

| Number | Pressure MPa | Temperature °C. | $CH_4$ | CO | $CO_2$ | $H_2$ | $O_2$ | $N_2 + Ar$ | $CH_3OH$ | $NH_3$ | $H_2O$ | Flow Rate Kmol/hr |
|---|---|---|---|---|---|---|---|---|---|---|---|---|
| 16 | 1.79 | 45 | 2.9 | 14.9 | 13.0 | 68.8 | | 0.2 | | | 0.2 | 18,358 |
| 17 | 7.05 | 240 | 18.8 | 7.2 | 10.0 | 62.3 | | 1.0 | 0.6 | | 0.1 | 119,369 |
| 18 | 7.00 | 265 | 20.4 | 5.5 | 9.0 | 57.3 | | 1.1 | 4.8 | | 2.0 | 110,129 |
| 20 | 6.78 | 45 | 21.7 | 5.8 | 9.5 | 61.1 | | 1.2 | 0.7 | | 0.1 | 103,230 |
| 21 | 6.78 | 45 | 21.7 | 5.8 | 9.5 | 61.1 | | 1.2 | 0.7 | | 0.1 | 101,011 |
| 22 | 6.78 | 45 | 21.7 | 5.8 | 9.5 | 61.1 | | 1.2 | 0.7 | | 0.1 | 2,219 |

TABLE 8

| Number | Pressure MPa | Temperature °C. | $CH_3OH$ | $NH_3$ | Others | $H_2O$ | Flow Rate t/day |
|---|---|---|---|---|---|---|---|
| 19 | 6.8 | 45 | 76.1 | | 3.9 | 19.4 | 4623 |

The invention claimed is:

1. A parallel process of coproducing methanol and ammonia using natural gas, liquid petroleum gas, butane or naphtha as a raw material, comprising the steps of:
introducing a first feedstream containing the raw material into a first reformer and performing steam-reforming of the first feedstream to form a first synthesis gas containing carbon monoxide, carbon dioxide and hydrogen;
reacting the first synthesis gas at a methanol synthesis pressure to form a mixture containing synthesized methanol and unreacted first synthesis gas in a methanol synthesis step;
condensing and gas-liquid separating the mixture containing synthesized methanol and unreacted first synthesis gas;
recovering hydrogen in a gas portion of the condensed and gas-liquid separated mixture which is rich in hydrogen from the unreacted first synthesis gas;
introducing a second feedstream containing the raw material into a primary reformer and performing steam-reforming of the second feedstream to form a second synthesis gas containing methane, carbon monoxide, carbon dioxide and hydrogen;
reforming unreformed methane remaining in the second synthesis gas with oxygen contained in air in a secondary reformer by partially combusting the second synthesis gas to provide the heat of reaction for the further reforming of the methane and form a crude synthesis gas containing carbon monoxide;
converting the carbon monoxide in the crude synthesis gas into carbon dioxide;
removing and recovering carbon dioxide from the crude synthesis gas;
subjecting the crude synthesis gas to a final purification by methanating traces of carbon monoxide and carbon dioxide remaining in the crude synthesis gas and separating a purge gas therefrom; and
synthesizing ammonia from the finally purified crude synthesis gas at an ammonia synthesis pressure;
and comprising the additional steps of:
adding the gas portion of the condensed and gas-liquid separated mixture which is rich in hydrogen to the crude synthesis gas contained carbon monoxide;
cooling the first synthesis gas;
separating and removing condensed water from the cooled first synthesis gas;
mixing the cooled first synthesis gas with the water separated and removed therefrom with carbon dioxide obtained by pre-compressing the carbon dioxide obtained in the carbon dioxide removing and recovering step to form a mixed synthesis gas;
compressing the mixed synthesis gas to the methanol synthesis pressure; and
supplying the compressed mixed synthesis gas for methanol synthesis in the methanol synthesis step.

2. The process of coproducing methanol and ammonia according to claim 1, wherein carbon monoxide and carbon dioxide are methanated to be inert to ammonia synthesis and other inert gas components which are introduced from the air used in the secondary reforming step, are further separated and removed by cryogenic separation in the final purifying step.

3. The process of coproducing methanol and ammonia according to claim 1, wherein a hydrogen permeable function membrane is used in the hydrogen recovering step.

4. The process of coproducing methanol and ammonia according to claim 1, wherein pressure swing adsorption is used in the hydrogen recovering step.

5. The process of coproducing methanol and ammonia according to claim 1, wherein a type of reactor for recovering the heat of reaction for methanol synthesis in the form of steam generation is used in the methanol synthesis step.

6. The process of coproducing methanol and ammonia according to claim 5, wherein a reactor provided with at least boiler tubes surrounded by a packed methanol synthesis catalyst and a center pipe for dispersion or collection of a reactant gas and having a configuration in which the reactant gas flows in catalyst layers in radial flow is used in the methanol synthesis step.

* * * * *